United States Patent
Haggblom et al.

(10) Patent No.: US 8,186,347 B2
(45) Date of Patent: May 29, 2012

(54) PATIENT BREATHING SYSTEM

(75) Inventors: Tom Jakob Haggblom, Vantaa (FI); Gustaf Jarnefelt, Espoo (FI)

(73) Assignee: General Electric Company, Schenectady, NY (US)

( * ) Notice: Subject to any disclaimer, the term of this patent is extended or adjusted under 35 U.S.C. 154(b) by 1007 days.

(21) Appl. No.: 12/143,096

(22) Filed: Jun. 20, 2008

(65) Prior Publication Data
US 2009/0000621 A1    Jan. 1, 2009

(30) Foreign Application Priority Data

Jun. 28, 2007    (EP) .................................... 07111222

(51) Int. Cl.
*A62B 19/00*    (2006.01)
(52) U.S. Cl. .......... 128/205.12; 128/205.27; 128/205.28
(58) Field of Classification Search ............. 128/205.12, 128/205.27–205.28
See application file for complete search history.

(56) References Cited

U.S. PATENT DOCUMENTS

| | | | |
|---|---|---|---|
| 5,471,979 A | 12/1995 | Psaros et al. | |
| 6,523,538 B1 * | 2/2003 | Wikefeldt | 128/204.18 |
| 7,762,255 B2 * | 7/2010 | Mills | 128/205.28 |
| 2001/0022179 A1 | 9/2001 | Kitten | |
| 2004/0003808 A1 | 1/2004 | Fuhrman | |
| 2007/0193584 A1 * | 8/2007 | Laurila et al. | 128/205.12 |

FOREIGN PATENT DOCUMENTS

| WO | WO 88/06904 A | 9/1988 |
|---|---|---|
| WO | WO 99/10034 | 3/1999 |

OTHER PUBLICATIONS

Database Medline (Online), US National Library of Medicine (NLM), Bethesda, MD, US: Mar. 1977 Jeal D E: "A Method of controlled ventilation with a circle-absorber breathing system", XP002458823, database accession No. NLM269740, vol. 49, No. 3, Mar. 1977, pp. 273-276, XP009092292, ISSN: 0007-0912.

George A. Gregory "Pediatric Anesthesia", 3rd edition, ISBN 0443089043, pp. 204-205 and 210-211 (1994).

* cited by examiner

*Primary Examiner* — Lynne Anderson
(74) *Attorney, Agent, or Firm* — Global Patent Operation; Jonathan E. Thomas

(57) ABSTRACT

A patient breathing system includes a ventilator that provides a driving gas flow to generate patient inspiration. The ventilator further includes a gas inlet for driving gas, the patient breathing system being connectable to a circle which includes an inspiratory hose and an expiratory hose connected to patient, through which circle expired gases can be circulated back to the patient. The circle further includes a fresh gas inlet, an arrangement for enabling the gas flow in a desired direction, a unit for removal of the exhaled carbon dioxide, and a ventilator port for the ventilator connection. The patient breathing system further includes an arrangement by which driving gas of the ventilator has been separated from the patient gases flowing in the circle.

20 Claims, 1 Drawing Sheet

PATIENT BREATHING SYSTEM

CROSS-REFERENCE TO RELATED APPLICATIONS

This application claims priority under 35 U.S.C. §119(a)-(d) to the filing date of earlier filed, co-pending European Patent Application Number 07 111 222.1, filed on Jun. 28, 2007, which is hereby incorporated by reference in its entirety.

BACKGROUND

1. Field of the Invention

The field of the invention relates to patient breathing systems generally, and more particularly, to a patient breathing system that includes a ventilator that provides driving gas flow to generate patient inspiration.

2. Description of Prior Art

As described above the invention relate to patient breathing systems. Patient breathing systems in anesthesia are classified as non-re-breathing and re-breathing breathing systems.

In non-re-breathing systems the gas mixture is supplied to the breathing system and inhaled directly by the patient. When the patient exhales all the exhaled gases are scavenged. The breathing system is very simple and reliable, but if expensive anesthetic inhaled drugs are used the non-re-breathing systems are very un-economical. The required fresh gas is the same as the minute volume for example for an adult about 6 l/min.

The re-breathing systems are divided into two subcategories either without or with carbon dioxide absorption.

In the re-breathing patient breathing systems without carbon dioxide absorption fresh gas is fed to the patient close to the airway. The exhaled gas moves in the ventilation hose toward the ventilator or manual ventilation bag. The fresh gas does not to a significant extent mix with the exhaled gas. In order for the patient gas to be separated from the driving gas of the ventilator there is usually either a descending or ascending bellows. In some ventilators the manual ventilation bag serves as a reservoir. During the expiratory pause the fresh gas flowing is further pushing the exhaled gas away from the patient and at the same time filling the ventilation hose with fresh gas for the next inspiration. Excess gas is scavenged through and pop-off valve. During the inspiration the fresh gas in the hose is first inspired and when that is used exhaled gas is inspired for a second time mixed together with the continuous flow of fresh gas. Re-breathing systems have been described by for example Mapleson and Bain in the book Pediatric anesthesia edited by George A. Gregory, $3^{rd}$ ed., ISBN 0-443-08904-3. A benefit of the re-breathing system without carbon dioxide absorption is that it is relatively simple. The consumption of fresh gas is somewhat lower than with a non-re-breathing system, the fresh gas required is approximately 50-75% of the minute volume.

The re-breathing patient breathing systems with carbon dioxide absorption are the most economical breathing systems where the fresh gas flow may be reduced to as low as the uptake of the patient. At the same time these systems are the most complex breathing systems. Basically this system comprises of a circle breathing system including a fresh gas inlet, inspiratory check valve, inspiratory hose, y-piece for patient connection, expiratory hose, expiratory check valve, ventilator connection and carbon dioxide absorber for removal of the exhaled carbon dioxide. The inspired gases consist of both new fresh gas and re-breathed exhaled gases from which the carbon dioxide has been removed. As new fresh gas is introduced to the breathing circuit some of the gas is taken up by the patient. The excess of gases is directed to the scavenging through the pop-off valve in the ventilator. In order for the patient gas to be separated from the driving gas (compressed air or oxygen) of the ventilator there is usually either a descending or ascending bellows. In some ventilators the manual ventilation bag serves as a reservoir and there might be either a piston or compressor in line as a ventilator. The consumption of fresh gas can in a circle breathing system be close to the uptake of gases, this can practically during the maintenance of the anesthesia be as low as less than 10% of the minute volume.

As the circle breathing systems are the most economical to use during inhaled anesthesia they are very common. At the same time the systems used are the most technically complex ones of the breathing systems. Complexity of the prior art systems leads to high demands for example in maintenance, which in turn leads to increases in costs. Owing to said facts high costs are one of the main disadvantages of the prior art.

The design of the ventilator is also quite challenging and it is difficult to design all the same ventilation modes as the bellows and pop-off valve causes disturbances and have to be considered when implementing the ventilation modes. This also leads to high costs.

Hospital infections are a big concern in today's world with the avian flu. The invention simplifies the cleaning of the breathing system as many parts are not required when compared to the systems of the prior art. The extended distance can be made as a disposable part, easy to clean and easily equipped with a microbe filter.

FIG. 1 shows schematically an example of a typical example of the breathing system of the prior art. Reference number 1 shows a patient and reference number 2 shows a ventilator. Reference number 3 shows an inspiratory hose and reference number 4 an expiratory hose. Reference number 5 shows a y-piece through which the inspiratory hose 3 and the expiratory hose 4 are connected to the patient. Reference number 6 shows a fresh gas inlet connected to the inspiratory hose.

The inspiratory hose 3 and the expiratory hose 4 form a circle through which expired gases can be circulated back to the patient. The circle formed by inspiratory hose 3 and the expiratory hose 4 are further provided with an arrangement for enabling the gas flow in a desired direction. Said arrangement can comprise inspiratory check valve 7 and an expiratory check valve 8 as shown in FIG. 1. Said arrangement can alternatively comprise a compressor, a fan, an ejector or some other appropriate arrangements. The circle comprises also a ventilator port 9 for the ventilator connection, and a unit for removal of the exhaled carbon dioxide. Said unit can be a carbon dioxide absorber 10 as shown in FIG. 1 or alternatively for example a membrane arrangement.

The patient breathing system comprises also an arrangement 11 by which driving gas of the ventilator 2 has been separated from the patient breathing gases flowing in the circle formed by the inspiratory hose 3 and the expiratory hose 4. In the example shown in FIG. 1 said arrangement is formed by a bellows or bag placed in a bottle. The bellows has typically a volume of about 2.5 litres and height of about 30 cm. The pipe between the bellows and the circle has typically a length of 1 m and a volume of 0.5 litre.

In the system shown in FIG. 1 the driving gas is in the space between the bellows and the bottle, and the patient gases are in the bellows, i.e. the bellows completely separates the driving gas from the patient gases.

Reference number 12 shows a pop-off valve through which the excess of gases is directed to scavenging.

The matters described above and operation of the system described in FIG. 1 are well known to a person skilled in the art.

The system shown in FIG. 1 has the disadvantages of the prior art described earlier in the text.

SUMMARY OF THE INVENTION

An embodiment of the invention addresses and/or eliminates these and/or other disadvantages of the prior art. In one embodiment of the invention, an arrangement separating the driving gas of the ventilator and the patient gases flowing in the circle is formed by an extended gas pathway between the circle and the ventilator.

An advantage of the invention is that the disadvantages of the bellows assembly can be eliminated, i.e. the complex systems of the prior art are considerably simplified. It must also be noticed that in anesthesia today the intravenous anesthesia is more and more common. The most optimal breathing system when using intravenous anesthesia is again the non-re-breathing breathing system. There is often a need to switch between the patient breathing systems in use. With embodiments of this invention it is easy to switch between both non-re-breathing and circle re-breathing patient breathing systems. In other words embodiments of the present invention offer great flexibility in practical care situations.

BRIEF DESCRIPTION OF THE DRAWINGS

In the following disclosure, embodiments of the invention will be described in detail by means of the examples shown in the attached drawing, in which.

DETAILED DESCRIPTION

Figure 1:
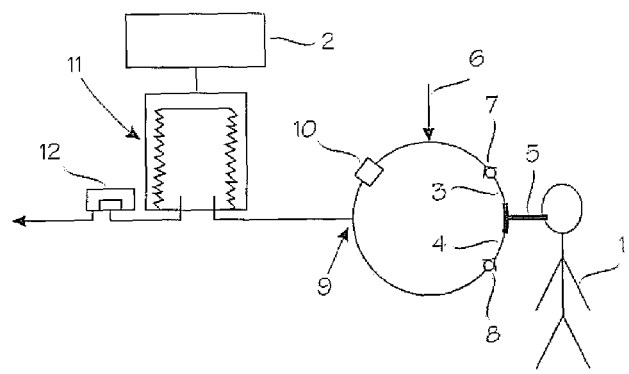
FIG. 1 shows schematically a typical example of the breathing system of the prior art.
Figure 2:
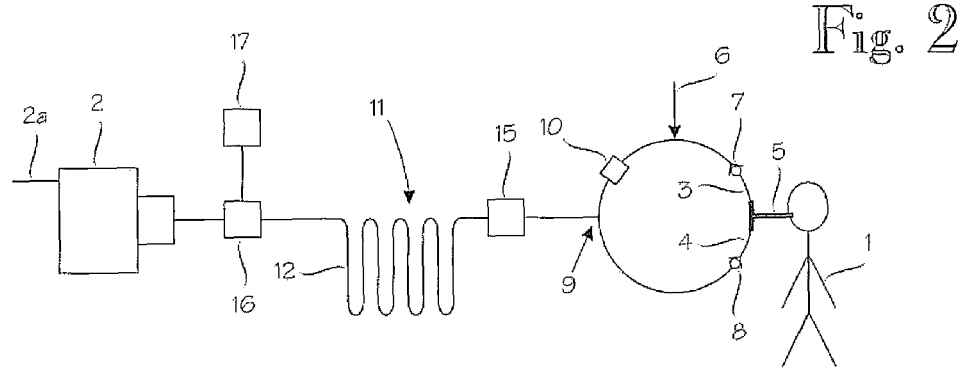
FIG. 2 shows schematically an embodiment of the breathing system of the invention.

FIG. 2 shows schematically one embodiment of system of the invention. In FIG. 2 same reference numbers are used in corresponding details as in FIG. 1. In FIG. 2 reference number 2a shows a gas inlet for driving gas. The gas flowing through inlet 2a can be for example air or oxygen or a mixture of air and oxygen. Driving gas can be pressurized gas or unpressurized, i.e. atmospheric gas.

An embodiment of the invention separates the circle breathing system from the ventilator with a long enough pathway 12. In other words embodiments of the present invention do not use a bellows or a bag in a bottle but the arrangement 11 by which the driving gas of the ventilator 2 has been separated from the patient breathing gases flowing in the circle formed at least partially by the inspiratory hose 3 and the expiratory hose 4 is formed by the extended gas pathway 12 between the circle and the ventilator. In embodiments of the invention there is an uninterrupted gas flow connection from gas inlet via ventilator to the patient.

As told earlier in the text the basic principle described above is used as such with the re-breathing systems without a carbon dioxide absorber where the fresh gas is staying relatively separate from the exhaled gas.

At least one distinguishing feature of an embodiment of the invention is that now the extended distance or pathway separates the circle and the ventilator. The volume of the extended pathway must be greater than the tidal breathing volume of the patient. This eliminates the need for having a membrane, for example a bellows, separating the patient gas from the driving gas in the ventilator. With a bellows the ventilation is not possible at all as long as the bellows is collapsed. In order for the user to restore ventilation after a disconnecting step the bellows needs to be filled with oxygen by pressing the oxygen flush button. As the bellows is removed with this invention it is not necessary to fill the bellows. The ventilation of the patient can be re-established immediately after the disconnecting step without further user interaction. If oxygen is used as the driving gas or if the ventilator can control the oxygen concentration the breathing system can automatically be filled with oxygen.

Figure 3:
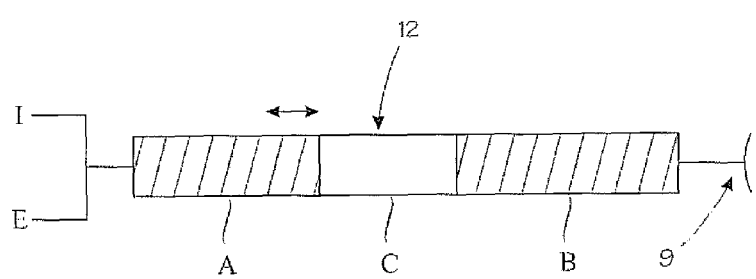
FIG. 3 shows schematically the basic principle used in the invention.

A basic operating principle of an embodiment of the invention is shown in FIG. 3. Inspiratory port of the ventilator is shown with a reference I and expiratory port of the ventilator is shown with a reference E. The extended pathway used in the invention is shown with reference number 12. Reference number 9 shows the ventilator port for the ventilator connection in the same way as in FIG. 2.

Area A in FIG. 3 shows a ventilator driving gas, area B shows patient exhaled gas and area C a border layer. According to the invention the extended gas pathway 12 separates the driving gas of the ventilator from the patient gases flowing in the circle formed by the inspiratory hose and the expiratory hose. The areas shown in FIG. 3 move to left and right according to the patients breathing steps. The length of the extended gas pathway is dimensioned so that the left end of the area B does not move in normal operation conditions to the right end of the pathway 12, and therefore the driving gas of the ventilator is not mixed with the patient breathing gases. Eventual leak in the circle can be noticed if the pressure is low and the right end of the area A moves to the right end of the pathway 12.

The length and the volume of the extended pathway may vary according to the existing needs, for example small babies may use an extended pathway having a length of at least about 3 m and a volume of at least 1500 ml if a tube having a diameter of 22 mm is used. Adults need a longer extended pathway, for example an extended pathway having a length of about 6 m and a volume of at least 2500 ml correspondingly. It is also possible to use other dimensions, for example middle size arrangement, i.e. an extended pathway having a length of about 4 m and a volume of at least 2000 ml can be used if needed.

The extended pathway 12 can be formed for example by using a flexible hose. Said flexible hose can be folded to form a waveform pathway.

Figure 4:
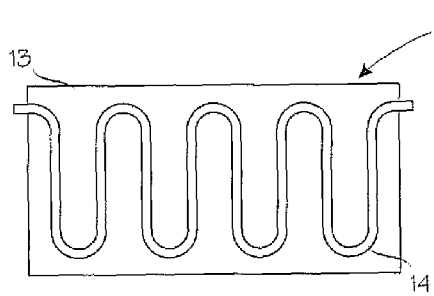
FIG. 4 shows an alternative embodiment of the extended pathway forming an essential part of the invention.

The extended pathway is not however limited to the use of flexible hose but the extended pathway can be materialized also by using a rigid structure having a waveform channel in it. FIG. 4 shows one example of said embodiment. Reference number 13 shows said rigid structure and reference number 14 said waveform channel. The rigid structure can be formed for example by moulding two halves from a plastic material and attaching said halves together to for a casing having the waveform channel mentioned extending through said casing.

FIG. 2 shows also some optional elements, which can be added to the system according to the invention. Reference number 15 shows a microbe filter, which can be placed between the extended gas pathway and the circle. Reference number 16 shows a valve via which an optional manual ventilation bag 17 can be connected to the system.

The embodiments described above are not intended to restrict the invention but only to clarify the basic idea of the invention. It is quite clear that details can be varied freely within the scope of the claims.

The invention claimed is:

1. A patient breathing system, comprising:
a ventilator configured to provide a driving gas flow to generate patient inspiration, the ventilator further including a gas inlet configured to drive gas;
a circle comprising an inspiratory hose and an expiratory hose that connect to a patient so expired gases can be circulated back to the patient, the circle also comprising a fresh gas inlet, an arrangement for enabling the gas flow in a desired direction, a unit for removal of the exhaled carbon dioxide, and a ventilator port for the ventilator connection; and
an extended gas pathway connected between the circle and the ventilator,
wherein the extended gas pathway separates the driving gas of the ventilator a the patient gases flowing in the circle, and
wherein the length of the extended gas pathway is at least about 3 m.

2. The system according to claim 1, wherein the extended pathway is formed by using a flexible hose.

3. The system according to claim 1, wherein the extended pathway is formed by a waveform channel in a rigid structure.

4. The patient breathing system according, to claim 1, wherein the extended pathway has a volume of at least 1500 ml.

5. The patient breathing system according to claim 1, wherein the extended pathway has a volume of at least 2000 ml.

6. The patient breathing system according to claim 1, wherein the extended pathway has a volume of approximately at least 2500 ml.

7. The patient breathing system according to claim 1, wherein between the extended gas pathway and the circle there is a microbe filter.

8. The patient breathing system according to claim 1, further comprising, a valve connected to the extended gas pathway and a manual ventilation bag connected to the valve.

9. The system according to claim 1, wherein the extended gas pathway has a volume that is greater than the tidal breathing volume of the patient.

10. A system to generate inspiration in a patient, said system comprising:
a ventilator;
an extended gas pathway connected to the ventilator; and
a circle connected to the extended gas pathway and to the patient, the circle comprising an inspiratory hose and an expiratory hose configured to circulate expired gases back to the patient,
wherein the extended as pathway provides uninterrupted as flow connection from the ventilator to the circle,
wherein the extended gas pathway comprises a flexible tube, and
wherein the flexible tube forms a waveform pathway.

11. The patient breathing system according to claim 10, further comprising a microbe filter between the extended gas pathway and the circle.

12. The system according to claim 10, wherein the extended gas pathway separates the ventilator from the circle a distance that prevents driving gas of the ventilator from mixing with the patient gas in the extended gas pathway.

13. A system for inspiration of a patient, said system comprising:
a ventilator;
an extended gas pathway connected to the ventilator; and
a circle connected to the extended gas pathway and to the patient, the circle comprising an inspiratory hose and an expiratory hose configured to circulate expired gases back to the patient,
wherein the extended gas pathway provides uninterrupted gas flow connection from the ventilator to the circle, and
wherein the extended gas pathway composes a waveform channel formed in a rigid structure.

14. The system according to claim 13, wherein the rigid structure comprises a casing with two halves that together form the waveform channel through the casing.

15. The system according to claim 13, wherein the extended gas pathway has a volume that is greater than the tidal breathing volume of the patient.

16. The system according to claim 13, wherein the extended gas pathway separates the ventilator from the circle a distance that prevents driving gas of the ventilator from mixing with the patient gas in the extended gas pathway.

17. The system according to claim 13, further comprising a microbe filter between the extended gas pathway and the circle.

18. The system according to claim 10, wherein the extended gas pathway has a volume that is greater than the tidal breathing volume of the patient.

19. The system according to claim 10, wherein the extended gas pathway separates the ventilator from the circle a distance that prevents driving gas of the ventilator from mixing with the patient gas in the extended gas pathway.

20. The system according to claim 10, further comprising a microbe filter between the extended gas pathway and the circle.

* * * * *